US011142562B2

(12) United States Patent
Prakash et al.

(10) Patent No.: US 11,142,562 B2
(45) Date of Patent: Oct. 12, 2021

(54) ANTIMICROBIAL PEPTIDE AND ITS USE THEREOF

(71) Applicant: Council of Scientific & Industrial Research, New Delhi (IN)

(72) Inventors: Balaji Prakash, Mysore (IN); Yashavanth Linganamane, Mysore (IN); Abhishek Acharya, Mysore (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 16/635,202

(22) PCT Filed: Sep. 22, 2017

(86) PCT No.: PCT/IN2017/050419
§ 371 (c)(1),
(2) Date: Jan. 30, 2020

(87) PCT Pub. No.: WO2017/221274
PCT Pub. Date: Dec. 28, 2017

(65) Prior Publication Data
US 2020/0255498 A1 Aug. 13, 2020

(30) Foreign Application Priority Data

Jul. 31, 2017 (IN) .............................. 201711027060

(51) Int. Cl.
| | |
|---|---|
| *A61K 38/00* | (2006.01) |
| *A61L 15/32* | (2006.01) |
| *C07K 14/81* | (2006.01) |
| *A01N 37/46* | (2006.01) |
| *A23L 3/3463* | (2006.01) |
| *C11D 3/48* | (2006.01) |

(52) U.S. Cl.
CPC ............ *C07K 14/811* (2013.01); *A01N 37/46* (2013.01); *A23L 3/3463* (2013.01); *A61K 38/00* (2013.01); *A61L 15/32* (2013.01); *C11D 3/48* (2013.01)

(58) Field of Classification Search
None
See application file for complete search history.

(56) References Cited

U.S. PATENT DOCUMENTS

| | | | |
|---|---|---|---|
| 5,217,717 A | 6/1993 | Kennedy et al. | |
| 5,981,722 A | 11/1999 | Chen et al. | |
| 7,217,690 B2 | 5/2007 | McGrath | |
| 8,394,941 B2 | 3/2013 | Amin et al. | |
| 2005/0075278 A1* | 4/2005 | McGrath .............. | C07K 14/811 514/18.7 |

FOREIGN PATENT DOCUMENTS

WO 0031139 A1 6/2000

OTHER PUBLICATIONS

Hersh et al, Clinical Infectious Diseases 2012;54(11):1677-8 (Year: 2012).*
CIDRAP News, Nov. 18, 2003, downloaded online on Nov. 25, 2020 from URL:<http://www.cidrap.umn.edu/news-perspective/2003/11/nih-launches-first-human-trial-ebola-vaccine> (Year: 2003).*
Mullin (Fierce Biotech, 2014), downloaded online on Nov. 25, 2020 from URL:<http://www.fiercebiotech.com/r-d/ebola-outbreak-rages-on-as-drug-development-remains-slow> (Year: 2014).*
"UpToDate", downloaded Mar. 24, 2021 from URL:< https://www.uptodate.com/contents/avoiding-infections-in-pregnancy-beyond-the-basics/print?source=see_link> (Year: 2021).*
Helmholtz (downloaded on Mar. 24, 2021 from URL:< https://www.helmholtz-hzi.de/en/news-events/stories/germ-time-safe-protection-against-infections/>) (Year: 2021).*
Needleman S.B. et al., "A general method applicable to the search for similarities in the amino acid sequence of two proteins," Journal of Molecular Biology, Academic Press, United Kingdom, vol. 48, No. 3, Mar. 28, 1970.
Li, et al., "Trypsin inhibitory loop is an excellent lead structure to design serine protease inhibitors and antimicrobial peptides," The FASEB Journal, 2007, pp. 2466-2473.
Adam Lesner et al., "Sunflower Trypsin Inhibitor 1 as a Molecular Scaffold for Drug Discovery," Current Pharmaceutical Design, vol. 17, No. 38, Dec. 1, 2011, pp. 4307-4317.
Adam Lesner et al., "Fluorescent analogs of trypsin inhibitor SFTI-1 isolated from sunflower seeds-synthesis and applications: Synthesis and Enzymatic Study of Trypsin Inhibitor," vol. 102, No. 1, Nov. 25, 2013, pp. 124-135.
Kalika Kuhar et al., "A Bowman-Birk protease inhibitor with antifeedant and antifungal activity from Dolichos biflorus," Acta Physiol Plant, 2013, pp. 1887-1903.
U. Malik et al, "In Vivo Efficacy of Anuran Trypsin Inhibitory Peptides against Staphylococcal Skin Infection and the Impact of Peptide Cyclization," Antimicrobial Agents and Chemotherapy, vol. 59, No. 4, Apr. 11, 2015.
International Search Report and Written Opinion dated Apr. 16, 2018 in related International Application No. PCT/IN2017/050419 filed Sep. 22, 2017.

* cited by examiner

*Primary Examiner* — Sergio Coffa
(74) *Attorney, Agent, or Firm* — Dinsmore & Shohl LLP

(57) ABSTRACT

The present invention relates to a novel peptide that exhibits effective antimicrobial activity against various gram-positive and gram-negative bacteria that are involved in food-borne pathogenesis, food spoilage and other pathogenic conditions. Therefore, this peptide can be a good candidate as antibacterial in agricultural, food and beverage industry, as well as for other medical applications and societal use.

9 Claims, 3 Drawing Sheets
Specification includes a Sequence Listing.

ANTIMICROBIAL PEPTIDE AND ITS USE THEREOF

FIELD OF THE INVENTION

The present invention relates to a novel peptide possessing antimicrobial activity. Particularly, the peptide design is inspired from Bowman-Birk family of trypsin inhibitors containing the trypsin inhibitory loop. The elements necessary for the desired properties (thermo-stability, membrane destabilization, and inhibition of serine proteases) were rationally incorporated based on an exhaustive analysis of naturally occurring antimicrobial peptides. This involved iterative experimental validation and design optimization till the best antimicrobial activity was obtained. The peptide demonstrates a very low hemolytic and cytotoxic activity and thereby can be used in food preservation and medical use. The peptide can be either chemically synthesized or produced by recombinant DNA technology.

BACKGROUND OF THE INVENTION

Every year the food industry faces huge economic losses, chiefly due to microbial food spoilage. Food spoilage is an area of global concern—as much as 25% of world production is lost post-harvest owing to microbial spoilage. The problem has been exacerbated due to the increasing population burden and international efforts of providing food security for all. It is therefore important to devise strategies for preventing microbial activity in food; anti-microbial peptides are considered promising candidates compared to traditional antibiotics and preservatives, since they are less toxic, have no special flavor and can be designed and synthesized easily. World over, there are concerted efforts to develop antimicrobial peptides. However, their use has largely been for clinical applications. It overlooks their application for other contexts, like to contain food spoilage. Although, use of antimicrobial peptides for preservation was suggested, there are no reports of exhaustive experimentation to demonstrate the same. Further, limitation of these preservatives is their restricted applicability due to their narrow range of pH and temperature stability; and in some cases, significant cytotoxicity too. This lead to the search for alternative molecules.

BBI (Bowman-Birk Inhibitors) constitute a class of highly stable small proteins (8,000 Da to 20,000 Da), due to their characteristically high Cys content. They contain a conserved nine-residue loop possessing protease inhibitory activity; this loop in BBIs could provide an ideal template for the design of inhibitors for food spoilage bacteria.

Various BBIs are currently being used for defense against insects. They are also used against cancer, allergic and inflammatory disorders, many cosmetic and medical applications. However, applications of BBIs for preventing food spoilage and food—borne diseases have not been sufficiently explored.

The growing demand for safer food preservation systems prompted us to develop novel antimicrobial peptides having best possible MIC values against diverse bacteria. We have successfully designed a series of effective anti-microbial peptide inhibitors which are inspired from BBIs that can be used in food preservation and other applications. Reference is made to the work of Ann R. Kennedy and Bernard F. Szuhaj, (1992), U.S. Pat. No. 5,217,717, which discloses a Bowman Birk Inhibitor concentrate (BBIC) and a method of preparation from soybean. It also provided a method for the administration of the said BBIC for inhibiting malignant transformation of cells and subsequent progression of cancer.

Reference is made to the work Ruzhu Chen et al., (1997), U.S. Pat. No. 5981722, which discloses a composition to control plant pests, specifically insects, by using the purified trypsin inhibitors from *Pentaclethra macrophylla* and *Pentaclethra macroloba* of leguminous family.

Reference is made to the work of Li J et al., (2007) showed that an undecapeptide loop derived from amphibian skin secretion possess a strong trypsin inhibitory activity. This peptide loop with a disulfide bridge is similar to the well-known trypsin inhibitory loop found in serine protease inhibitors. A series of synthetic peptides based on this peptide also showed good trypsin inhibitory activity.

Reference is made to the work of Kalika Kuhar et al., (2013), reported a Bowman-Birk Inhibitor from *Dolichos biflorus* plant, which shows antifungal activity against several phytopathogenic fungi and antifeedant activity. The work did not report its activity against any bacteria.

Reference is made to the work of Kevin P. McGrath, (2003), U.S. Pat. No. 7,217,690 B2, discloses small cyclic peptides related to Sunflower Trypsin Inhibitor-1, compositions and articles that can inhibit or prevent skin irritation caused by proteolytic activity. This work makes use of the protease inhibition properties of these peptides. The present cyclic peptides are effective against a number of proteases, including serine proteases such as trypsin, chymotrypsin, cathepsin G, elastase, matripase, thrombin and the like.

Reference is made to the work of Neelam S. Amin et al., (2011), U.S. Pat. No. 8,394,941 B2, discloses modified variant Bowman-Birk protease inhibitory proteins (BBPIs), compositions containing BBPIs, methods for making and using the modified variant BBPIs for personal care.

Reference is made to the work of Robert leo Brady et al., (1999), patent no. WO200031139A1, discloses peptides which mimic the serine protease binding loop of Bowman-Birk inhibitors and pharmaceutical composition comprising those peptides. In many cases, the limitations of the proposed peptides in terms of their properties (pH, temperature stability and cytotoxicity) and antimicrobial efficacy is not discussed. In others, the applicability of these peptides for prevention of food spoilage and food preservation have not been addressed.

OBJECTIVE OF THE INVENTION

Figure 1:
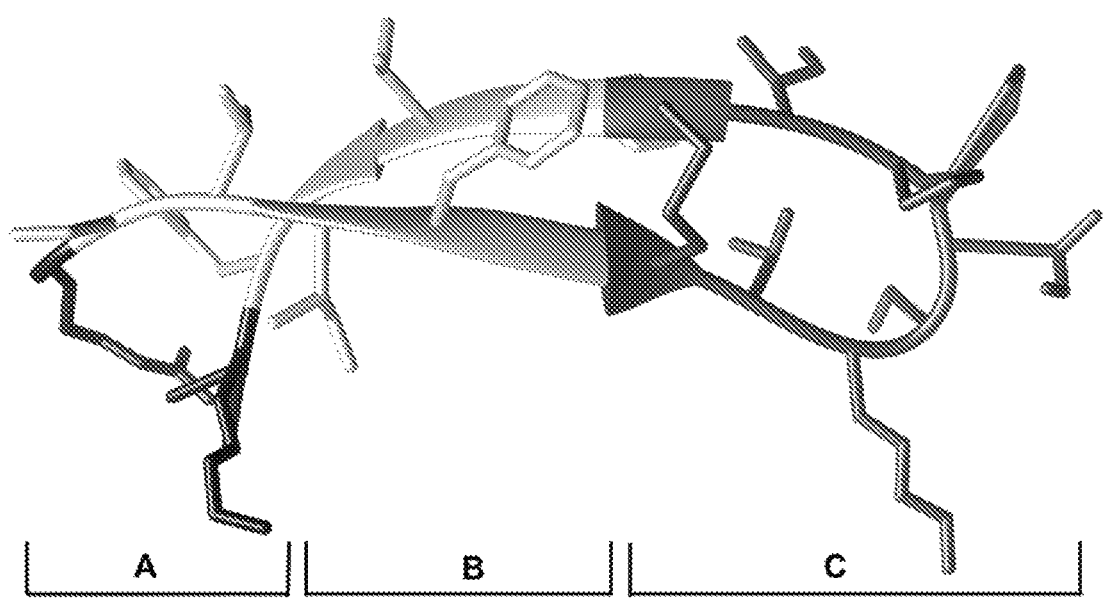
FIG. 1. Three dimensional structure of $Pep^{20}$. Region [A] represents the charged amino acids, region [B] represents the residues following the cysteines on either side which include hydrophobic amino acids and region [C] represents the trypsin inhibitory loop.

The main object of the present invention is to provide an antimicrobial peptide, which is used in food preservation and related applications and medical use.

Another object of the present invention is to alter, enhance or preserve the efficacy of the designed peptide by making peptide variants.

Yet another object of the present invention is to inhibit the food spoiling microorganisms using the designed peptide and/or those derived based on the 2$^{nd}$ object of the invention. Yet another object of the present invention is the application of the peptides included in the above claims as a combination/cocktail of two or more individual peptides, derived from the 2$^{nd}$ object of the invention or otherwise, and their simultaneous use with other antimicrobial agents.

Yet another object of the present invention is simultaneous inhibition of more than one critical microbial target (serine proteases and bacterial membrane).

SUMMARY OF THE INVENTION

Accordingly, the present invention provides a novel antimicrobial peptide for diverse applications having the following general formula An anti-microbial peptide having general formula:

$$B[B_1..B_m]GCTKSIPPIC[B_1..B_n]Y$$

wherein

m and n can independently range from 2 to 8 amino-acid residues;

X, Y is Arginine or Lysine;

B is an Amino acid selected from the group consisting of Serine, Threonine, Isoleucine, Leucine, Valine, Phenylalanine, Tyrosine, Tryptophan, Cysteine, Arginine, and Lysine.

Optionally if B is a cysteine on either side, additional disulphide bridges are incorporated for enhanced stability.

The peptide comprises of at least one disulphide bridge as illustrated in the designs. Additional disulphide bridges could be incorporated in designs derived from the parent peptide formula.

The present embodiment of the invention provides an anti-microbial peptide, wherein sequence of the anti-microbial peptide is selected from the group consisting of sequences having SEQ ID No. 1 to 20 or a variant of said amino acid sequence, said variant having >80% homology with sequences having SEQ ID No. 1 to 20.

In yet another embodiment the invention provides an antimicrobial peptide wherein peptide variant is mutated by a method selected from the group consisting of substitution of one or more amino acids, deletion of one or more amino acids, and insertion of one or more amino acids.

In another embodiment the invention provides a mechanism for simultaneous inhibition of more than one critical microbial target (serine proteases and bacterial membrane).

In another embodiment the invention provides a method of inhibiting the bacteria, using combination of two or more individual peptides.

The present invention provides a design for novel antimicrobial peptides inspired by Bowman-Birk Inhibitors. Three representative peptides are provided below for proof of principle.

```
Sequence ID 1 (Pep20)-
RSVIFGCTKSIPPICFVGFK
(Disulfide- cys 7 to cys 15)

Sequence ID 2 (Pep19)-
SVIFGCTKSIPPICFVGFK
(Disulfide- cys 6 to cys 14)

Sequence ID 3 (Pep16)-
SVIGCTKSIPPICFVK
(Disulfide- cys 5 to cys 13)
```

DETAILED DESCRIPTION OF THE INVENTION

The present invention relates to a novel antimicrobial peptide useful in food preservation and other applications The peptide proposed as a part of the main object of the invention consists of the following structural features (FIG. 1):

a) A trypsin inhibitory loop with a hairpin structure stabilized by a disulphide bridge.

b) Amino acids sequence on both ends of, i.e. N- and C-terminal to the trypsin inhibitory loop consisting of predominantly hydrophobic amino acids.

c) Basic residues towards N- and C-terminal ends.

d) In context of three-dimensional structure of the peptide, the presence of disulphide-bridge causes the peptide portions at either end of the trypsin inhibitory loop to come in close proximity to form a hydrophobic patch.

e) The basic residue at the termini and the lysine from the trypsin inhibitory loop maintains an overall positive charge in the peptide.

In the context of the antimicrobial activity of the peptide, the aforesaid structural features have the following functions.

Trypsin inhibitory loop: Serves to inhibit extracellular and intracellular serine proteases produced by bacteria for its defense and survival.

Disulphide bridge: Responsible for structural stability of the peptide in a hairpin conformation. This also imparts thermostability to the peptide.

Basic residues: In the three-dimensional hairpin structure of the peptide, the basic residues at the two terminals and the lysine at the trypsin inhibitory loop form an amphiphilic structure wherein the positively charged ends of the hairpin interact with the negatively charged phosphate moiety of the phospholipid bilayer, while the hydrophobic core interacts with the lipid chains. The positive charge also serves to drive the binding of the peptides specifically to bacterial membranes that have a predominantly negative charge due to 23% phosphatidylglycerol content.

Twenty representative peptides are provided below.

Sequence ID 1-
RSVIFGCTKSIPPICFVGFK
(Disulfide- cys 7 to cys 15)

Sequence ID 2-
SVIFGCTKSIPPICFVGFK
(Disulfide- cys 6 to cys 14)

Sequence ID 3-
SVIGCTKSIPPICFVK
(Disulfide- cys 5 to cys 13)

Sequence ID 4-
RSFIFGCTKSIPPICFVGFK
(Disulfide- cys 7 to cys 15)

Sequence ID 5-
RSVIFGCTKSIPPICFVGTR
(Disulfide- cys 7 to cys 15)

Sequence ID 6-
RSVIFGCTKSIPPICFVGFRR
(Disulfide- cys 7 to cys 15)

Sequence ID 7-
RSIIFGCTKSIPPICVFGFRR
(Disulfide- cys 7 to cys 15)

Sequence ID 8-
RRTFIGCTKSIPPICVGFR
(Disulfide- cys 7 to cys 15)

Sequence ID 9-
RRVVFCTKSIPPICFFRR
(Disulfide- cys 6 to cys 14)

Sequence ID 10-
RSFGCVIFGCTKSIPPICFVGFCFVR
(Disulfide- cys 5 to cys 15,
Disulfide- cys 10 to cys 23)

Sequence ID 11-
RRFICVIFGCTKSIPPICFVGFCIFRR
(Disulfide- cys 5 to cys 23,
Disulfide- cys 10 to cys 18)

Sequence ID 12-
RRVIFGCTKSIPPICFVGFRR
(Disulfide- cys 7 to cys 15)

Sequence ID 13-
RRLIFLCTKSIPPICFVFVGFR
(Disulfide- cys 7 to cys 15)

Sequence ID 14-
RRLFGVCTKSIPPICFLGIRR
(Disulfide- cys 7 to cys 15)

Sequence ID 15-
RSRSVIFGCTKSIPPICFVGFSR
(Disulfide- cys 9 to cys 17)

Sequence ID 16-
RFRFRCTKSIPPICRFRFR
(Disulfide- cys 6 to cys 14)

Sequence ID 17-
RSRSCVGIFCTKSIPPICGFGFCRSR
(Disulfide- cys 5 to cys 23,
Disulfide- cys 10 to cys 18)

Sequence ID 18-
RSRSKFLGCTKSIPPICFFGRSR
(Disulfide- cys 9 to cys 17)

Sequence ID 19-
RSRSKFLGCTKSIPPICFFGVRSR
(Disulfide- cys 9 to cys 17)

Sequence ID 20-
RTRSVIFGCTKSIPPICFVGFRSR
(Disulfide- cys 9 to cys 17)

EXAMPLES

The following examples are given by way of illustration of the present invention and therefore should not be construed to limit the scope of the present invention.

Example 1: Design and Process of Making the Peptide

For the design of antimicrobial peptide, we started out with the sequence and structure analysis of naturally available peptides. We identified structural motifs that may possess a particular activity. For example, the trypsin inhibitory motif [CTKSIPPIC] has serine protease inhibitory activity, wherein the presence of disulfides impart thermostability, and presence of hydrophobic and charged cationic residues in the peptide aids interaction with bacterial membranes. The key idea was to assemble these motifs into a single peptide, i.e distinct regions within the same peptide performing different function. For this work, we used the β-hairpin peptide of the bowman-birk inhibitor class of serine protease inhibitors. This class already has the trypsin inhibitory loop, and addition to hydrophobic and cationic residue segments allowed the incorporation of multiple properties into a single peptide. The assembly of these distinct motifs (each with specific properties) into a single peptide can be represented by the formula claimed in claim 1 and depicted in FIG. 1. This formula can act as a general guideline for the design of β-hairpin forms of cationic antimicrobial peptides.

Once the peptide sequences are derived from the above formula, the peptides can be artificially synthesized or produced by recombinant DNA based methods. For our studies, all the peptides were synthesized by solid phase synthesis (Fmoc chemistry) and purified by high performance liquid chromatography using a commercial peptide synthesizing service. The synthetic peptide production and purifications methods are conventional hence detailed description is omitted.

Example 2. Antimicrobial Assays

Antimicrobial assays against various bacterial cultures were done using the micro dilution broth assay according to the Clinical and Laboratory Standards Institute. Four Gram-positive bacteria; *Listeria monocytogenes* ATCC13932, *Bacillus cereus* ATCC11778, *Staphylococcus aureus* ATCC12900, *Micrococcus luteus* ATCC4698 and Five Gram-negative bacteria; *Escherichia coli* ATCC11775, *Pectobacterium carotovorum* MCC2112, *Klebsiella pneumoniae* MTCC4032, Pseudomonas aeruginosa MTCC4673 and *Salmonella typhimurium* ATCC9844 were used in this study. All ATCC strains were procured from the American Type Culture Collection (ATCC, Manassas, Va., USA). All MTCC strains were procured from Microbial Type Culture Collection (MTCC, Chandigarh, India). All MCC strains were procured from Microbial Culture collection (MCC, Pune, India). Mueller-Hinton broth was used to dilute the peptide stock and the bacterial inoculum. Inoculum was prepared from the mid logarithmic phase culture. Each well of the microtiter plates received aliquots of 100 μL of the media containing different concentrations of peptide ranging from 0.3 to 300 μg/mL. In each wells final concentration of bacteria was $5\times10^5$ CFU/mL. Peptides were tested in duplicates. To validate the assay, untreated growth control and a positive control with a known antimicrobial were included. Microtiter plates were incubated at 37° C. for 5-6 hours with continuous shaking at 130 RPM. MIC was determined by visually observing the color change by adding Resazurin dye into each well at a final concentration of 37 μg/100 μL. Here, MIC is defined as the lowest concentration of peptide that completely inhibited the growth of the organism. MIC values for two peptides, Pep$^{20}$ and Pep$^{19}$ are shown in Table 1.

TABLE 1

| SN | Micro Organisms | Pep$^{20}$MIC (μg/mL) | Pep$^{19}$MIC (μg/mL) |
|---|---|---|---|
| 1 | Listeria onocytogenes | 50 | >150 |
| 2 | Bacillus cereus | 12.5 | 75 |
| 3 | Staphylococcus aureus | 150 | >150 |
| 4 | Micrococcus luteus | 1.25 | 6.25 |
| 5 | Escherichia coli | 150 | >150 |
| 6 | Pectobacterium Carotovoumr | 50 | 150 |
| 7 | Salmonella tphimurium | 85 | >150 |

Example 3: Scanning Electron Microscopy

Figure 2:
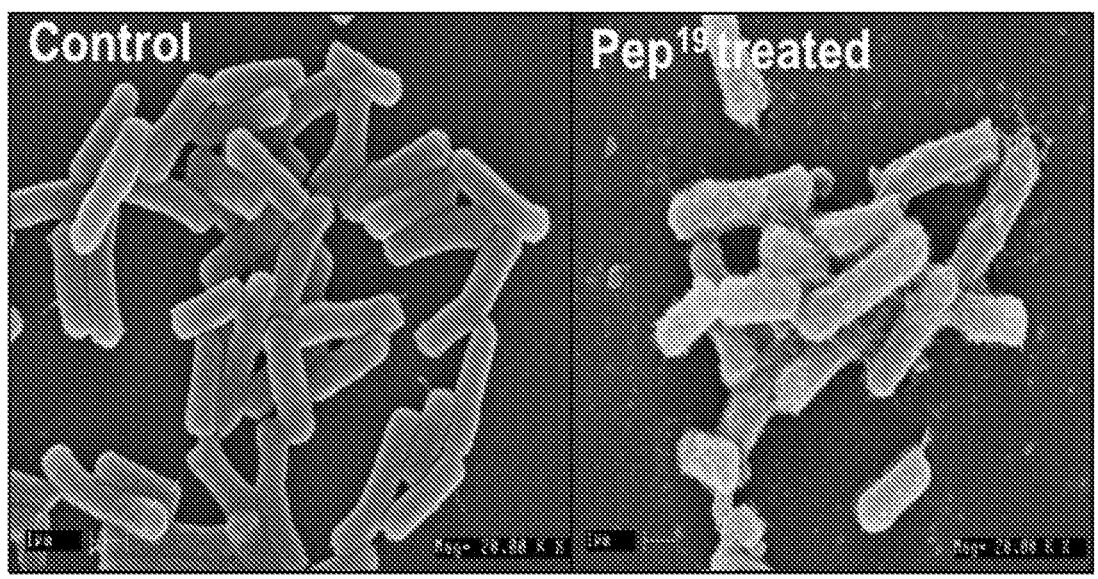
FIG. 2. Scanning Electron Microscopy (SEM) Images of B. cereus treated with $pep^{19}$ at 2× MIC concentration—Cell morphology and membrane integrity of *B. cereus* cells were observed by using SEM after treating the cells with $Pep^{19}$. Membrane surface of the peptide treated cells became roughened, lost integrity and intracellular content leakage was observed. Peptide untreated control cells were bright with a smooth surface, membrane was intact and the cells were devoid of such alterations, suggesting the peptides act on the bacterial cell membrane.

For sample preparation, *B. cereus* cells were grown in LB broth at 37° C. to mid log phase under continuous shaking at 180 RPM. Cells were harvested by centrifugation at 5,500 RPM for 5 min, washed thrice with 10 mM PBS (phosphate buffer saline), diluted $1\times10^8$ CFU/mL with PBS. Cells were incubated with 2× MIC of peptide in a 500 μL reaction for 1 hour. Control cells were incubated without peptides. After incubation cells were harvested by centrifugation at 8,000 RPM for 5 min, washed thrice with PBS, fixed with 2.5% (w/v) glutaraldehyde at room temperature for 4 hours, followed by washing twice with PBS. The cells were dehydrated for 10 min with a graded ethanol series (25%, 50%, 75%, 95%, and 100%). Pellet was dissolved in 100% ethanol and dried. The samples were mounted on the specimen holder and sputter-coated with gold. Samples were transferred to electron microscope (LEO 435 VP, USA) and observed. Results showed that the bacterial plasma membrane was thoroughly disrupted by the peptide (FIG. 2).

Example 4: Membrane Permeabilization

Figure 3:
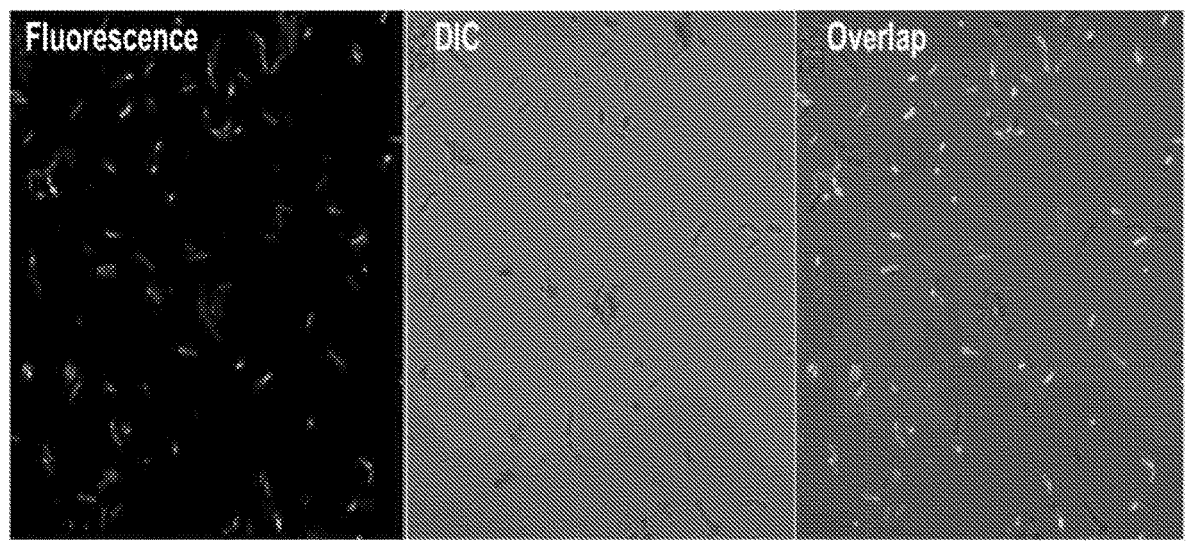
FIG. 3. Confocal Microscopic Images of *B. cereus* treated with FITC-$pep^{19}$—For the determination of site of action, bacterial cells treated for 1 hour with FITC tagged $Pep^{19}$ at 1× MIC, appeared as green rods with fluorescence spread all over the bacterial cell indicating the internalization of the peptide.

For the determination of site of action and localization of the designed peptides, *B. cereus* and *M. luteus* cells in mid-logarithmic phase were harvested by centrifugation, washed three times with 10 mM PBS, pH 7.2.×$10^7$ CFU/mL cells were incubated with FITC labeled peptide at 1× MIC concentration at 37° C. for 1 hour. After 1 hour, cells were pelleted down and washed 3 times with PBS and spotted on a glass slide and observed under a confocal microscope (LSM700, Carl Zeiss, Germany). Fluorescent images were obtained with a 488 nm band-pass filter for excitation of FITC. It was observed that FITC-labeled peptides were internalized into the cytoplasm of the bacteria, causing cell damage (FIG. 3).

Example 5: Hemolytic and Cytotoxicity Studies

This example shows that peptides are non-hemolytic and non-cytotoxic. The hemolytic activity of the peptide was evaluated using human red blood cells (hRBCs). Erythrocytes were separated from 1 mL of blood by centrifugation at 1,500 rpm for 10 min. washed hRBCs were washed 3 times with PBS, diluted to 4% (v/v) in PBS. 100 μL of the hRBCs having peptides ranging from 4 to 200 μg/mL as added into 96 wells microtiter plate. The plates were incubated for 1 h at 37° C. without agitation and centrifuged at 1,500 RPM for 5 min. Aliquots (100 μl) of the supernatant were transferred to 96-well plates and absorbance was measured at 414 nm. PBS and 1% Triton-X 100 were used as control for 0% and 100% hemolysis. At a concentration range from 4 to 200 μg/mL, peptides demonstrated a hemolytic effect at a level below 2%.

Cytotoxicity was measured using WST assay. ARPE-19 (Retinal pigmented epithelial) cells, chosen to represent human cells, growing in log phase were seeded into 96 wells cell-culture plates at $4\times10^4$ the cells were incubated at 37° C. for 24 hours under 5% $CO_2$. Peptide is added at concentrations of 4 to 200 μg/mL in DMEM/F12 nutrient mixture media for the treatment group, whereas for the negative control group, media alone was added. The cells were incubated for 16 hours at 37° C. under 5% CO2. 10 μL of WST-1 reagent was added into each well. Plate was incubated at 37° C. for 2 hours. Color intensity was measured at 450 nm. Cell viability was higher than 80% at a peptide concentration ranging from 4 to 120 μg/mL. Even at concentrations up to 200 μg/mL, cell viability was still nearly 70%, suggesting low cytotoxicity of peptides. These data indicate that designed peptides are biocompatible.

Example 6: Trypsin Inhibition

The amidase activity of trypsin and its inhibition was assayed using the chromogenic substrate BAPNA at pH 8.2 in 0.05 M Tris-HCl containing 0.02 M $CaCl_2$ at 37° C. The assay reaction contained 50 μL of trypsin solution (40-50 μg of trypsin in 1 mM HCl), 50 μL of water and 125 μL of the substrate. The reaction was carried out at 37° C. for 10 min and stopped by addition of 0.25 mL of 30% acetic acid. Absorbance of the liberated p-nitroaniline was measured at 410 nm against an appropriate blank in which the reaction was arrested by adding 30% acetic acid prior to BAPNA addition.

The trypsin solution was incubated with an aliquot of inhibitor for 10 min at 37° C. and reaction was started by the addition of 125 μL substrate and incubated at 37° C. for 10 min. The reaction was arrested by addition of 30% acetic acid and the residual trypsin activity was measured by recording the absorbance at 410 nm. All the tested peptides showed good inhibition against trypsin.

Example 7: pH and Thermostability

Thermostability was measured by the determination of protease inhibition activity of the peptides after incubation for 30, 60, 90, 120, 150 and 180 minutes at 95° C. All the tested peptides retained more than 50% of their activity even after heating at 95° C. Peptides were dissolved in 50 mM buffers of pH 2.5, 5, 9 and incubated for 2 h at room temperature. Protease inhibition activity of the peptides was assayed using the BAPNA method described earlier. Peptides were found to be stable at the tested pH range.

Advantages of the Invention

The designed peptide of the invention shows very less hemolytic activity and cytotoxicity.
The designed peptide of the invention shows very high stability at wide range of temperatures and pH.
The designed peptide of the invention is resistant to cleavage against serine proteases.
The designed peptide of the invention is short and can be easily synthesized chemically or may be produced by recombinant DNA technology.

The designed peptide of the invention has been tested against wide range of microorganisms and shows antimicrobial activity.

It is cost effective.

We claim:

1. A thermo-stable anti-microbial peptide having the general formula:

$$B[B_1..B_m]GCTKSIPPIC[B_1..B_n]Y$$

wherein

denotes a disulphide bridge;
- m and n independently range from 2 to 8 amino-acid residues;
- X, Y is Arginine or Lysine;
- each B is an Amino acid selected from the group consisting of Serine, Threonine, Isoleucine, Leucine, Valine, Phenylalanine, Tyrosine, Tryptophan, Cysteine, Arginine, and Lysine, and
- wherein the thermo-stable anti-microbial peptide comprises an amino acid sequence selected from the group consisting of SEQ ID NOs: 1 to 20.

2. The thermo-stable anti-microbial peptide of claim 1, wherein the thermo-stable anti-microbial peptide comprises more than one disulphide bridge.

3. A therapeutic composition comprising a therapeutically effective amount of the thermo-stable anti-microbial peptide of claim 1, and a pharmaceutically acceptable carrier.

4. A disinfecting solution comprising the thermo-stable anti-microbial peptide of claim 1.

5. A food preservative comprising the thermo-stable anti-microbial peptide of claim 1.

6. A biomedical device comprising the thermo-stable anti-microbial peptide of claim 1.

7. A sanitary pad, aseptic clothing, or bandage comprising the thermo-stable anti-microbial peptide of claim 1.

8. A method of treating an infection caused by microorganism in a subject in need thereof, wherein the microorganism is selected from *Listeria* onocytogenes, *Bacillus cereus, Staphylococcus aureus, Micrococcus luteus, Escherichia coli, Pectobacterium carotovoumr*, and *Salmonella* tphimurium, and wherein the method comprises administering a therapeutically effective amount of a composition to the subject, the composition comprising the thermo-stable anti-microbial peptide of claim 1, and a pharmaceutically acceptable carrier.

9. The method of claim 8, wherein the thermo-stable anti-microbial peptide is administered singly or in combination.

* * * * *

```
                              SEQUENCE LISTING

<160> NUMBER OF SEQ ID NOS: 20

<210> SEQ ID NO 1
<211> LENGTH: 20
<212> TYPE: PRT
<213> ORGANISM: Artificial sequence
<220> FEATURE:
<223> OTHER INFORMATION: Generated from formula 1

<400> SEQUENCE: 1

Arg Ser Val Ile Phe Gly Cys Thr Lys Ser Ile Pro Pro Ile Cys Phe
1               5                   10                  15

Val Gly Phe Lys
            20

<210> SEQ ID NO 2
<211> LENGTH: 19
<212> TYPE: PRT
<213> ORGANISM: Artificial sequence
<220> FEATURE:
<223> OTHER INFORMATION: Generated from formula 1

<400> SEQUENCE: 2

Ser Val Ile Phe Gly Cys Thr Lys Ser Ile Pro Pro Ile Cys Phe Val
1               5                   10                  15

Gly Phe Lys

<210> SEQ ID NO 3
<211> LENGTH: 16
<212> TYPE: PRT
<213> ORGANISM: Artificial sequence
<220> FEATURE:
<223> OTHER INFORMATION: Generated from formula 1

<400> SEQUENCE: 3

Ser Val Ile Gly Cys Thr Lys Ser Ile Pro Pro Ile Cys Phe Val Lys
1               5                   10                  15

<210> SEQ ID NO 4
<211> LENGTH: 20
<212> TYPE: PRT
<213> ORGANISM: Artificial sequence
<220> FEATURE:
<223> OTHER INFORMATION: Generated from formula 1

<400> SEQUENCE: 4

Arg Ser Phe Ile Phe Gly Cys Thr Lys Ser Ile Pro Pro Ile Cys Phe
1               5                   10                  15

Val Gly Phe Lys
            20

<210> SEQ ID NO 5
<211> LENGTH: 20
<212> TYPE: PRT
<213> ORGANISM: Artificial sequence
<220> FEATURE:
<223> OTHER INFORMATION: Generated from formula 1

<400> SEQUENCE: 5
```

```
Arg Ser Val Ile Phe Gly Cys Thr Lys Ser Ile Pro Pro Ile Cys Phe
1               5                   10                  15

Val Gly Thr Arg
            20

<210> SEQ ID NO 6
<211> LENGTH: 21
<212> TYPE: PRT
<213> ORGANISM: Artificial sequence
<220> FEATURE:
<223> OTHER INFORMATION: Generated from formula 1

<400> SEQUENCE: 6

Arg Ser Val Ile Phe Gly Cys Thr Lys Ser Ile Pro Pro Ile Cys Phe
1               5                   10                  15

Val Gly Phe Arg Arg
            20

<210> SEQ ID NO 7
<211> LENGTH: 21
<212> TYPE: PRT
<213> ORGANISM: Artificial sequence
<220> FEATURE:
<223> OTHER INFORMATION: Generated from formula 1

<400> SEQUENCE: 7

Arg Ser Ile Ile Phe Gly Cys Thr Lys Ser Ile Pro Pro Ile Cys Val
1               5                   10                  15

Phe Gly Phe Arg Arg
            20

<210> SEQ ID NO 8
<211> LENGTH: 19
<212> TYPE: PRT
<213> ORGANISM: Artificial sequence
<220> FEATURE:
<223> OTHER INFORMATION: Generated from formula 1

<400> SEQUENCE: 8

Arg Arg Thr Phe Ile Gly Cys Thr Lys Ser Ile Pro Pro Ile Cys Val
1               5                   10                  15

Gly Phe Arg

<210> SEQ ID NO 9
<211> LENGTH: 18
<212> TYPE: PRT
<213> ORGANISM: Artificial sequence
<220> FEATURE:
<223> OTHER INFORMATION: Generated from formula 1

<400> SEQUENCE: 9

Arg Arg Val Val Phe Cys Thr Lys Ser Ile Pro Pro Ile Cys Phe Phe
1               5                   10                  15

Arg Arg

<210> SEQ ID NO 10
<211> LENGTH: 26
<212> TYPE: PRT
<213> ORGANISM: Artificial sequence
<220> FEATURE:
<223> OTHER INFORMATION: Generated from formula 1

<400> SEQUENCE: 10
```

-continued

```
Arg Ser Phe Gly Cys Val Ile Phe Gly Cys Thr Lys Ser Ile Pro Pro
1               5                   10                  15

Ile Cys Phe Val Gly Phe Cys Phe Val Arg
            20                  25

<210> SEQ ID NO 11
<211> LENGTH: 27
<212> TYPE: PRT
<213> ORGANISM: Artificial sequence
<220> FEATURE:
<223> OTHER INFORMATION: Generated from formula 1

<400> SEQUENCE: 11

Arg Arg Phe Ile Cys Val Ile Phe Gly Cys Thr Lys Ser Ile Pro Pro
1               5                   10                  15

Ile Cys Phe Val Gly Phe Cys Ile Phe Arg Arg
            20                  25

<210> SEQ ID NO 12
<211> LENGTH: 21
<212> TYPE: PRT
<213> ORGANISM: Artificial sequence
<220> FEATURE:
<223> OTHER INFORMATION: Generated from formula 1

<400> SEQUENCE: 12

Arg Arg Val Ile Phe Gly Cys Thr Lys Ser Ile Pro Pro Ile Cys Phe
1               5                   10                  15

Val Gly Phe Arg Arg
            20

<210> SEQ ID NO 13
<211> LENGTH: 22
<212> TYPE: PRT
<213> ORGANISM: Artificial sequence
<220> FEATURE:
<223> OTHER INFORMATION: Generated from formula 1

<400> SEQUENCE: 13

Arg Arg Leu Ile Phe Leu Cys Thr Lys Ser Ile Pro Pro Ile Cys Phe
1               5                   10                  15

Val Phe Val Gly Phe Arg
            20

<210> SEQ ID NO 14
<211> LENGTH: 21
<212> TYPE: PRT
<213> ORGANISM: Artificial sequence
<220> FEATURE:
<223> OTHER INFORMATION: Generated from formula 1

<400> SEQUENCE: 14

Arg Arg Leu Phe Gly Val Cys Thr Lys Ser Ile Pro Pro Ile Cys Phe
1               5                   10                  15

Leu Gly Ile Arg Arg
            20

<210> SEQ ID NO 15
<211> LENGTH: 23
<212> TYPE: PRT
<213> ORGANISM: Artificial sequence
<220> FEATURE:
<223> OTHER INFORMATION: Generated from formula 1

<400> SEQUENCE: 15
```

Arg Ser Arg Ser Val Ile Phe Gly Cys Thr Lys Ser Ile Pro Pro Ile
1               5                   10                  15

Cys Phe Val Gly Phe Ser Arg
            20

<210> SEQ ID NO 16
<211> LENGTH: 19
<212> TYPE: PRT
<213> ORGANISM: Artificial sequence
<220> FEATURE:
<223> OTHER INFORMATION: Generated from formula 1

<400> SEQUENCE: 16

Arg Phe Arg Phe Arg Cys Thr Lys Ser Ile Pro Pro Ile Cys Arg Phe
1               5                   10                  15

Arg Phe Arg

<210> SEQ ID NO 17
<211> LENGTH: 26
<212> TYPE: PRT
<213> ORGANISM: Artificial sequence
<220> FEATURE:
<223> OTHER INFORMATION: Generated from formula 1

<400> SEQUENCE: 17

Arg Ser Arg Ser Cys Val Gly Ile Phe Cys Thr Lys Ser Ile Pro Pro
1               5                   10                  15

Ile Cys Gly Phe Gly Phe Cys Arg Ser Arg
            20                  25

<210> SEQ ID NO 18
<211> LENGTH: 23
<212> TYPE: PRT
<213> ORGANISM: Artificial sequence
<220> FEATURE:
<223> OTHER INFORMATION: Generated from formula 1

<400> SEQUENCE: 18

Arg Ser Arg Ser Lys Phe Leu Gly Cys Thr Lys Ser Ile Pro Pro Ile
1               5                   10                  15

Cys Phe Phe Gly Arg Ser Arg
            20

<210> SEQ ID NO 19
<211> LENGTH: 24
<212> TYPE: PRT
<213> ORGANISM: Artificial sequence
<220> FEATURE:
<223> OTHER INFORMATION: Generated from formula 1

<400> SEQUENCE: 19

Arg Ser Arg Ser Lys Phe Leu Gly Cys Thr Lys Ser Ile Pro Pro Ile
1               5                   10                  15

Cys Phe Phe Gly Val Arg Ser Arg
            20

<210> SEQ ID NO 20
<211> LENGTH: 24
<212> TYPE: PRT
<213> ORGANISM: Artificial sequence
<220> FEATURE:
<223> OTHER INFORMATION: Generated from formula 1

<400> SEQUENCE: 20

```
Arg Thr Arg Ser Val Ile Phe Gly Cys Thr Lys Ser Ile Pro Pro Ile
1               5                   10                  15
Cys Phe Val Gly Phe Arg Ser Arg
                20
```